United States Patent
Wada et al.

(10) Patent No.: US 8,278,108 B2
(45) Date of Patent: Oct. 2, 2012

(54) AUTOMATIC ANALYZER

(75) Inventors: Kentaro Wada, Hitachinaka (JP); Katsuhiro Kambara, Hitachinaka (JP); Tetsuji Kawahara, Hitachinaka (JP); Hidenobu Komatsu, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/145,801

(22) PCT Filed: Jan. 22, 2010

(86) PCT No.: PCT/JP2010/000346
§ 371 (c)(1),
(2), (4) Date: Aug. 10, 2011

(87) PCT Pub. No.: WO2010/087137
PCT Pub. Date: Aug. 5, 2010

(65) Prior Publication Data
US 2011/0283779 A1    Nov. 24, 2011

(30) Foreign Application Priority Data
Jan. 29, 2009   (JP) ................................. 2009-017455

(51) Int. Cl.
*G01N 1/00* (2006.01)
*G01N 1/10* (2006.01)
*G01N 35/10* (2006.01)
*B01L 3/02* (2006.01)

(52) U.S. Cl. .............. 436/43; 436/47; 436/180; 422/63; 422/67; 422/68.1; 73/61.59; 73/863.01

(58) Field of Classification Search ..................... 422/63, 422/67, 68.1; 73/61.59, 863.01; 436/43, 436/47, 180
See application file for complete search history.

(56) References Cited

U.S. PATENT DOCUMENTS

| | | | |
|---|---|---|---|
| 5,876,668 A * | 3/1999 | Kawashima et al. | 422/64 |
| 7,205,158 B2 * | 4/2007 | Pankratz et al. | 436/180 |
| 7,341,691 B2 * | 3/2008 | Tamura et al. | 422/64 |
| 2003/0049171 A1 | 3/2003 | Tamura et al. | |
| 2011/0271773 A1 * | 11/2011 | Komatsu et al. | 73/863.01 |
| 2012/0046203 A1 * | 2/2012 | Walsh et al. | 506/39 |

FOREIGN PATENT DOCUMENTS

| | | |
|---|---|---|
| JP | 3-25368 A | 2/1991 |
| JP | 5-80059 A | 3/1993 |
| JP | 7-98320 A | 4/1995 |
| JP | 8-101216 A | 4/1996 |
| JP | 8-194004 A | 7/1996 |
| JP | 9-145718 A | 6/1997 |
| JP | 2003-83988 A | 3/2003 |

* cited by examiner

*Primary Examiner* — Nikita Wells
(74) *Attorney, Agent, or Firm* — Mattingly & Malur, PC

(57) ABSTRACT

An automatic analyzer of the type equipped with a sample preprocessing function pretreats a desired sample in a pretreating unit before pipetting the sample into an analyzing unit for analysis. When all samples are carried to the analyzing unit via the pretreating unit, irrespective of whether the sample is to be pretreated, this causes loss in terms of both costs and installation space requirements. In the case where the preprocessing is required, a minimal quantity of the sample is also necessary in order to make the sample react to the preprocessing liquid. In addition, the possible presence of a residual sample left in the pretreating unit could affect analytical results. The automatic analyzer which includes an analyzing unit and a pretreating unit further includes a sample-pipetting mechanism constructed to have a function that allows the mechanism to access a plurality of pipetting positions without a sample sucking/discharging position being fixed.

6 Claims, 5 Drawing Sheets

AUTOMATIC ANALYZER

TECHNICAL FIELD

The present invention relates generally to automatic analyzers that performs qualitative and quantitative analysis of biological samples such as blood and urine, and more particularly, to an automatic analyzer with a mechanism for diluting samples.

BACKGROUND ART

Automatic analyzers are widely known in the field of clinical laboratory tests. Mechanisms that pipet the samples, reagents, and preprocessing liquids used for these kinds of analytical operations, have traditionally been divided into several types according to purpose, such as for sample use, for reagent use, and for preprocessing liquid use. Sample sucking/discharging positions in these sampling mechanisms (in other words, pipetting mechanisms) are fixed, irrespective of the kind and purpose of analysis requested. Pretreating a sample refers to mixing the sample with a preprocessing liquid before starting the analysis to render the sample analyzable. The use of a preprocessing liquid to dilute a sample for reduced concentration also allows relative reduction in the consumption of the reagents used for causing reactions.

Automatic analyzers equipped with a preprocessing disk to pipet such a preprocessing liquid are described in, for example, Patent Documents 1 to 4.

Prior Art Literature
Patent Documents
  Patent Document 1: JP-1996-101216-A
  Patent Document 2: JP-1995-098320-A
  Patent Document 3: JP-1993-080059-A
  Patent Document 4: JP-1991-25368-A

SUMMARY OF THE INVENTION

Problems to be Solved by the Invention

Proposed automatic analyzers of the type equipped with a sample preprocessing function pretreat a desired sample in a pretreating unit before pipetting the sample into an analyzing unit for analysis. In such a conventional type of automatic analyzer, all samples are carried to the analyzing unit via the pretreating unit, irrespective of whether the sample is to be pretreated. Analysis of a sample not requiring the preprocessing, therefore, does not require the pretreating unit itself and thus causes loss in terms of both costs and installation space requirements. In the case where the preprocessing is required, a minimal quantity of sample is also necessary in order to make the sample react to a preprocessing liquid. In addition, the possible presence of a residual sample left in the pretreating unit could affect analytical results.

Means for Solving the Problems

In order to solve the above problems, the present invention provides the following configurations:

An automatic analyzer including an analyzing unit and a pretreating unit according to an aspect of the present invention further includes a sample-pipetting mechanism constructed to have a function that allows the mechanism to access a plurality of pipetting positions without a sample sucking/discharging position being fixed. For example, in an apparatus configuration including at least one sample-pipetting mechanism 1 to suction from a sample transport unit a sample not to be pretreated and pipet the suctioned sample in a pretreating unit, and further including at least one sample-pipetting mechanism 2 to suction from the sample transport unit a sample to be pretreated and pipet the suctioned sample in an analyzing unit, the sample to be pretreated and the sample not to be pretreated can be pipetd in the analyzing unit by assigning to the sample-pipetting mechanism 2 a function that suctions from the sample transport unit the sample not to be pretreated and pipets the suctioned sample in the analyzing unit.

EFFECTS OF THE INVENTION

In the automatic analyzer according to the present invention, a sample to be pretreated and a sample not to be pretreated are selectively pipetd in the analyzing unit according to the analytical items requested. When the number of samples to be analyzed is relatively small, one pipetting mechanism can pipet both of the with and without preprocessing samples, whereas when the number of samples is relatively large, at least two pipetting mechanisms can each pipet either the former or latter sample. The sample from the sample transport unit is pipetd directly in the analyzing unit, so that an original quantity of sample is minimized, whereby any impacts caused by a residual sample left in the pretreating unit to analytical results are controlled to an ignorable level. In addition, since the sample is made to directly react with a reagent while maintaining a concentration of the sample, analytical results are easy to digitize, with no necessity arising to enhance sensitivity of the assay apparatus.

MODES FOR CARRYING OUT THE INVENTION

Figure 1:
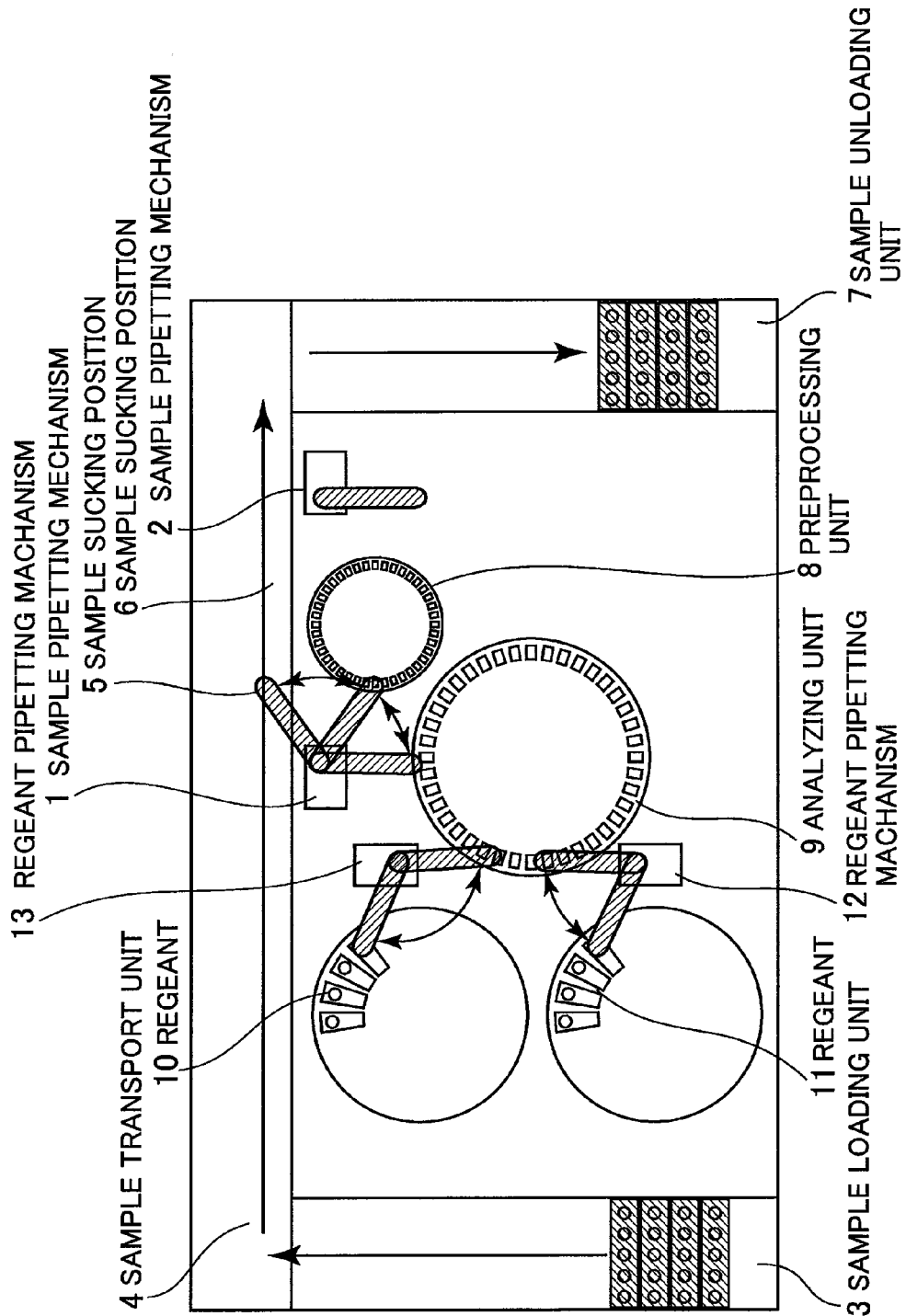
FIG. 1 is a schematic diagram of an automatic analyzer which implements type 1 of embodiment of the present invention.
Figure 2:
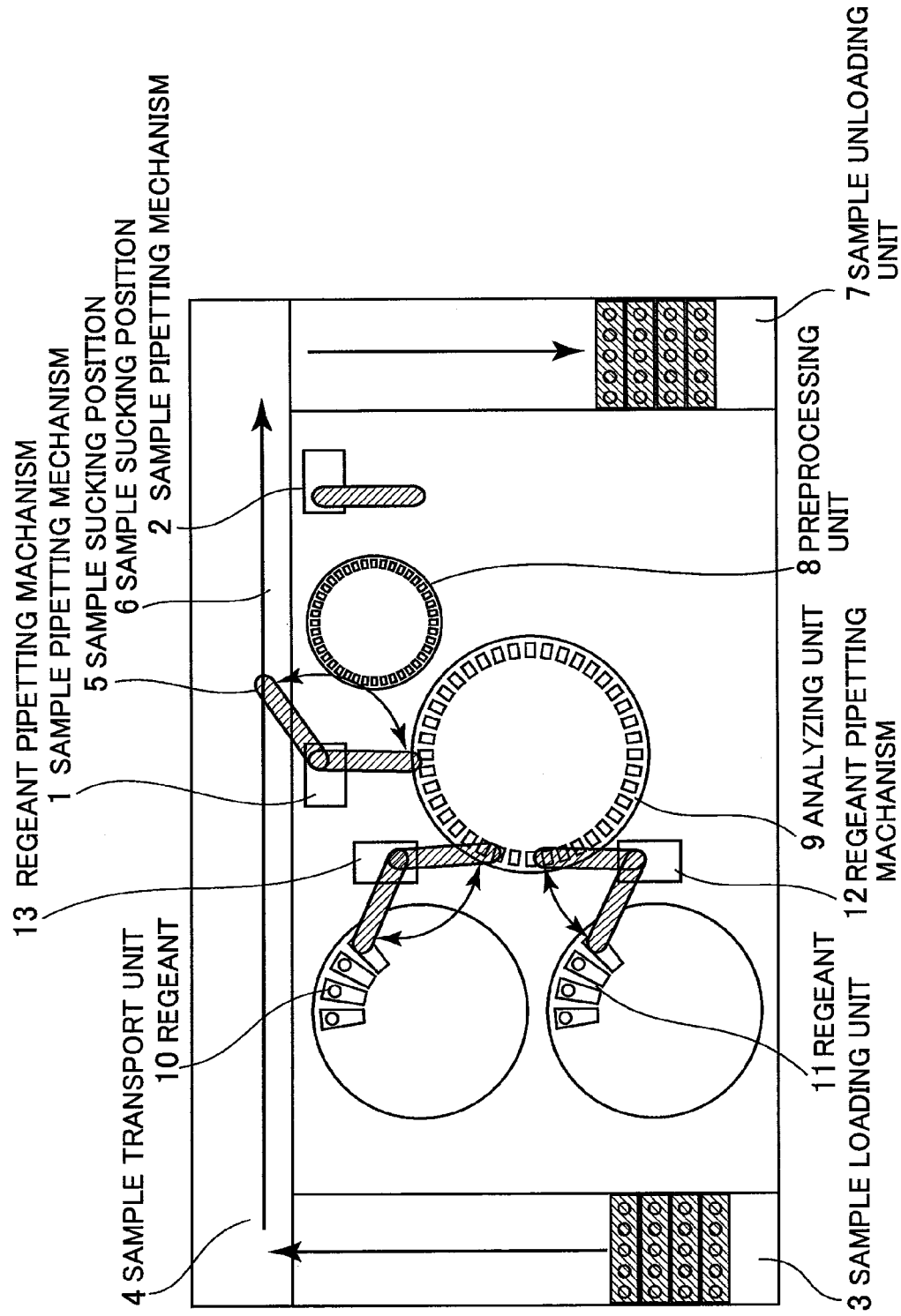
FIG. 2 is a schematic diagram of an automatic analyzer which implements type 2 of embodiment of the present invention.
Figure 3:
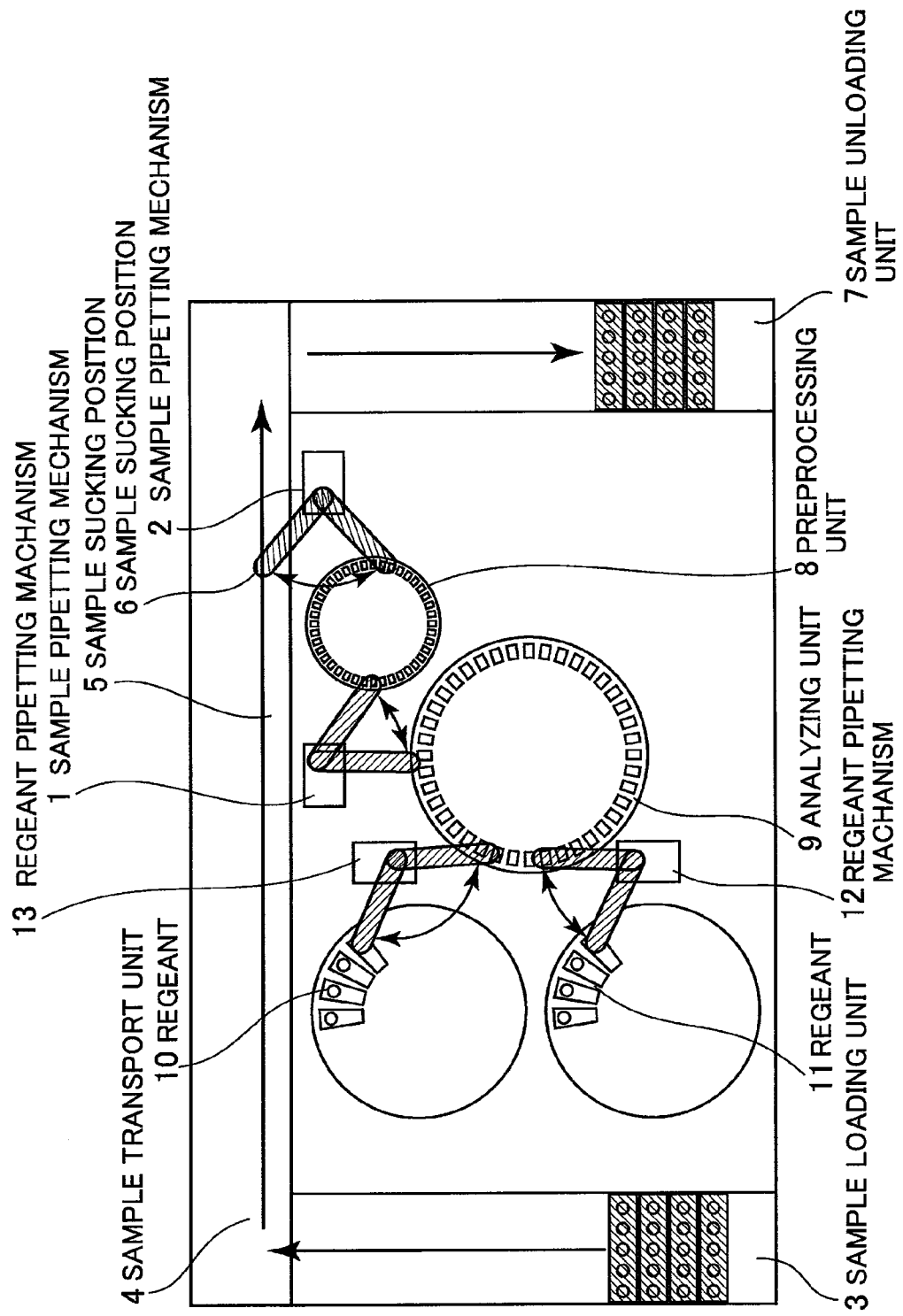
FIG. 3 is a schematic diagram of an automatic analyzer which implements type 3 of embodiment of the present invention.
Figure 4:
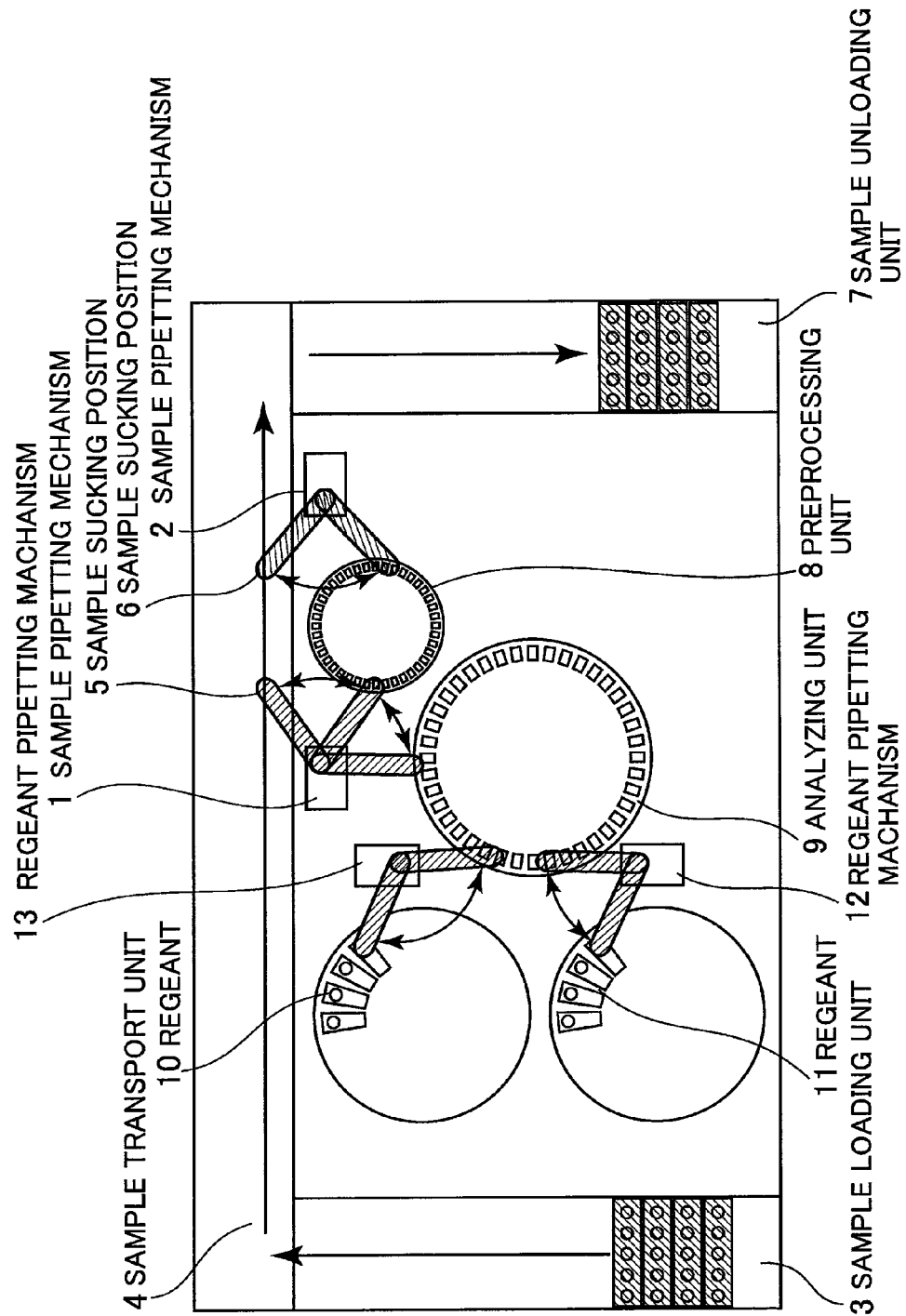
FIG. 4 is a schematic diagram of an automatic analyzer which implements type 4 of embodiment of the present invention.

Hereunder, embodiments of the present invention will be described using the accompanying drawings.

FIGS. 1 to 4 show examples of apparatus configurations including a pipetting function according to the present invention. Each of the apparatus configurations includes a sample-pipetting mechanism 1, a sample-pipetting mechanism 2, a sample-loading unit 3, a sample transport unit 4, a sample suction position 5, a sample suction position 6, a sample unloading unit 7, a pretreating unit 8, an analyzing unit 9, a reagent 10, a reagent 11, a reagent-pipetting mechanism 12, and a reagent-pipetting mechanism 13. Process flow of analysis in the automatic analyzer according to the present invention is described below for each of the four apparatus configurations independently.

Type 1 (FIG. 1):

First, an operator puts samples to be tested, in the sample-loading unit 3. Each sample then enters a waiting state for analysis. Upon a start of the analysis, the sample transport unit 4 carries the sample to the sample suction position 5 at which the sample-pipetting mechanism 1 then suctions the sample and pipets the suctioned sample into the pretreating unit 8. After preprocessing of the sample at the pretreating unit 8, the sample-pipetting mechanism 1 suctions the pretreated sample from the pretreating unit 8 and pipets the sample into the analyzing unit 9. In this way, the analyzer can pipet a pretreated sample into the analyzing unit 9. After the pipetting, the reagent-pipetting mechanisms 12 and 13 respectively pipet the corresponding reagents 11 and 10 into the analyzing unit 9, then mix the reagents with the sample, and generate reactions to obtain analytical results.

Advantages of type 1 are described below. In the present type, the sample-pipetting mechanism 1 moves the sample from the sample transport unit 4 through the pretreating unit 8 to the analyzing unit 9. In this operational sequence, pipetting a pretreated sample into the analyzing unit 9 can be conducted with one pipetting mechanism. Since operation of the sample-pipetting mechanism 2 can be omitted, therefore, operational simplification, cost reduction, and space saving are achieved. For these reasons, when the number of samples is relatively small and each sample is to be pretreated, the present type is desirably used to conduct analyses.

Type 2 (FIG. 2):

As in type 1, each sample in the sample-loading unit 3 is carried by the sample transport unit 4 and stops at the sample suction position 5. At this position, the sample-pipetting mechanism 1 suctions the sample and after passing through the pretreating unit 8, pipets the sample into the analyzing unit 9. In this way, the analyzer can pipet a non-pretreated sample into the analyzing unit 9. After the pipetting, the reagent-pipetting mechanisms 12 and 13 respectively pipet the corresponding reagents 11 and 10 into the analyzing unit 9, then mix the reagents with the sample, and generate reactions to obtain analytical results.

Advantages of type 2 are described below. In the present type, the sample-pipetting mechanism 1 moves the sample from the sample transport unit 4 through the pretreating unit 8 (but skips the sample through the pretreating unit 8) to the analyzing unit 9. In this operational sequence, pipetting a non-pretreated sample into the analyzing unit 9 can be conducted with one pipetting mechanism. Since the operation of the sample-pipetting mechanism 2 can be omitted, therefore, operational simplification, cost reduction, and space saving are achieved. For these reasons, when the number of samples is relatively small and sample preprocessing is to be skipped, the present type is desirably used to conduct analyses.

Type 3 (FIG. 3):

Each sample in the sample-loading unit 3, as in types 1 and 2, is carried by the sample transport unit 4 and stops at the sample suction position 6. At this position, the sample-pipetting mechanism 2 suctions the sample and then pipets the sample into the pretreating unit 8. After preprocessing of the sample at the pretreating unit 8, the sample-pipetting mechanism 1 suctions the pretreated sample from the pretreating unit 8 and pipets the sample into the analyzing unit 9. After the pipetting, the reagent-pipetting mechanisms 12 and 13 respectively pipet the corresponding reagents 11 and 10 into the analyzing unit 9, then mix the reagents with the sample, and generate reactions to obtain analytical results.

Advantages of type 3 are described below. In the present type, the sample-pipetting mechanism 2 moves the sample from the sample transport unit 4 to the pretreating unit 8. After this, the sample-pipetting mechanism 1 moves the sample from the pretreating unit 8 to the analyzing unit 9. In this operational sequence, upon the sample-pipetting mechanism 2 carrying the sample from the sample transport unit 4 to the pretreating unit 8, the sample-pipetting mechanism 1 carries the sample from the pretreating unit 8 to the analyzing unit 9. A pretreated sample can thus be pipetd into the analyzing unit 9. The two pipetting mechanisms operate in cooperative association with each other. Compared with type 1, therefore, the present type reduces a pipetting cycle time in the analyzing unit 9 and improves throughput. In addition, since the pipetting mechanism for the samples requiring the preprocessing is driven independently of the pipetting mechanism for samples not requiring the preprocessing, any effects of pipetting mechanism usage upon the possible presence of a residual sample can be ignored. For these reasons, when the number of samples is relatively large and sample preprocessing is required, the present type is desirably used to conduct analyses.

Type 4 (FIG. 4):

The samples disposed in the sample-loading unit 3 are carried by the sample transport unit 4 and stop at the sample suction positions 5 and 6. At these positions, the sample-pipetting mechanisms 1 and 2 suction the samples and then pipet them into the pretreating unit 8. After preprocessing of the samples at the pretreating unit 8, the sample-pipetting mechanism 1 suctions the pretreated samples from the pretreating unit 8 and pipets the samples into the analyzing unit 9. After the pipetting, the reagent-pipetting mechanisms 12 and 13 respectively pipet the corresponding reagents 11 and 10 into the analyzing unit 9, then mix the reagents with each pipetd sample independently, and generate reactions to obtain analytical results.

Advantages of type 4 are described below. In the present type, the sample-pipetting mechanisms 1 and 2 move individual samples from the sample transport unit 4 to the pretreating unit 8. Additionally, the sample-pipetting mechanism 1 moves one of the samples from the pretreating unit 8 to the analyzing unit 9. In this operational sequence, the sample-pipetting mechanisms 1 and 2 each carry one sample from the sample transport unit 4 to the pretreating unit 8 simultaneously and independently, and the sample-pipetting mechanism 1 carries the sample from the pretreating unit 8 to the analyzing unit 9. Pretreated samples can thus be pipetd into the analyzing unit 9. The two pipetting mechanisms operate in cooperative association with each other. Compared with type 3, therefore, the present type reduces a pipetting cycle time in both of the pretreating unit 8 and the analyzing unit 9, thereby improving throughput. Transport line to the pretreating unit 8, in particular, takes place through two routes and hence improves efficiency in a case of an increase in the number of kinds of preprocessing operations such as dilution and mixing.

For these reasons, when the number of samples is relatively large and sample preprocessing is required, the present type is desirably used to conduct analyses.

The present invention provides the configurations that enable the four types of operation described above. During a request for analytical items, the operator who operates the automatic analyzer of any one of these configurations can select whether the preprocessing is to be performed upon the sample. In accordance with the analysis request conditions, the apparatus determines the mode to operate from among the four types, and then operates in that mode for the highest achievable efficiency.

Figure 5:
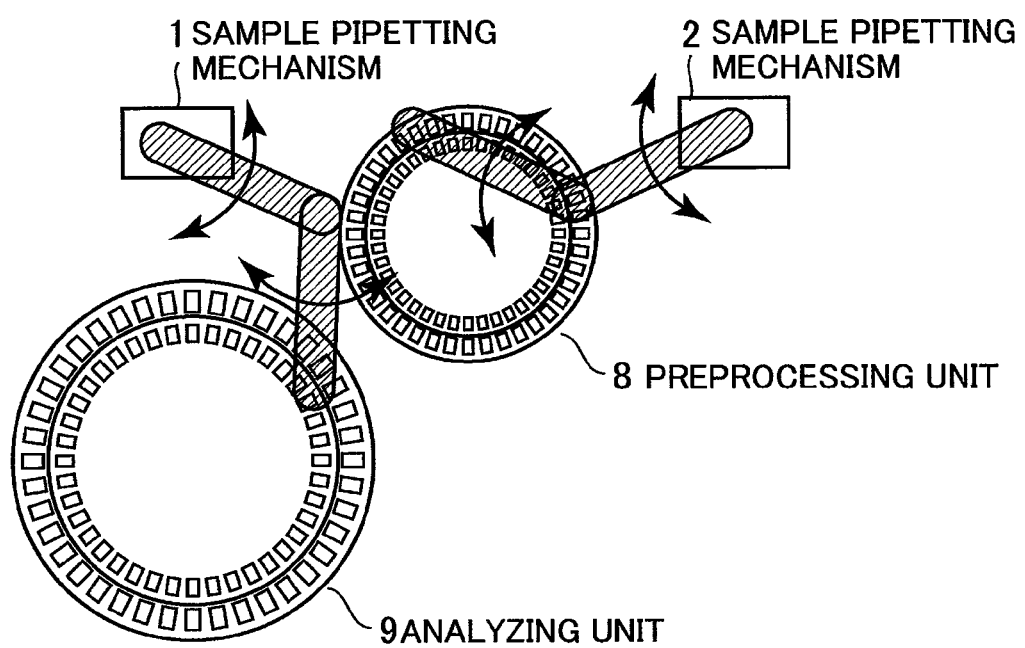
FIG. 5 is a schematic diagram of sample-pipetting mechanisms each having two axes of rotation in the present invention.

Providing at least two axes of rotation in rotational drives of each of the sample-pipetting mechanisms 1 and 2, as shown in FIG. 5, enhances operational flexibility of both mechanisms without limiting respective access points to positions on orbits. This enables accessing, even if the pretreating unit 8 and the analyzing units 9 are formed into a multiple-ring structure including more than one unit each. Therefore, sample-pipetting positions increase and any effects of a residual sample upon analytical results become less significant. Throughput improves under an arrangement of multiple sample-pipetting mechanisms, in particular.

Appropriate layout and space saving are also realized since placement positions for any cleaning agents, preprocessing liquids, and control samples suctioned and discharged by the sample-pipetting mechanisms, are not limited.

DESCRIPTION OF REFERENCE NUMBERS 1, 2 Sample-pipetting mechanism
3 Sample-loading unit
4 Sample transport unit
5, 6 Sample suction position
7 Sample unloading unit
8 Pretreating unit
9 Analyzing unit
10, 11 Reagent
12, 13 Reagent-pipetting mechanism

The invention claimed is:

1. An automatic analyzer comprising:
 a sample container for accommodating a sample;
 a mechanism for retaining the sample container;
 a preprocessing container for adding a preprocessing liquid to the sample pipetd from the sample container;
 a mechanism for retaining the preprocessing container;
 a reaction cuvette for mixing the sample and a reagent;
 a mechanism for retaining the reaction cuvette; and
 a first sample-pipetting mechanism for pipetting the sample from both of the sample container retained by the sample container retaining mechanism, and the preprocessing container retained by the preprocessing container retaining mechanism, into the reaction cuvette retained by the reaction cuvette retaining mechanism.

2. The automatic analyzer according to claim 1, wherein:
 the preprocessing container retaining mechanism is provided between the sample container retaining mechanism and the reaction cuvette retaining mechanism.

3. The automatic analyzer according to claim 2, further comprising in addition to the first sample-pipetting mechanism:
 a second sample-pipetting mechanism for pipetting the sample from the sample container retained by the sample container retaining mechanism, into the preprocessing container retained by the preprocessing container retaining mechanism.

4. The automatic analyzer according to claim 3, wherein:
 positions at which the first sample-pipetting mechanism and the second sample-pipetting mechanism execute sample pipetting from the sample container retained by the sample container retaining mechanism are not limited.

5. The automatic analyzer according to claim 1, wherein:
 the sample container retaining mechanism is a sample rack.

6. The automatic analyzer according to claim 1, wherein:
 the preprocessing liquid is a dilute solution.

* * * * *